US010500150B2

(12) United States Patent
Matsuo et al.

(10) Patent No.: US 10,500,150 B2
(45) Date of Patent: Dec. 10, 2019

(54) ELASTIC JELLY-LIKE COMPOSITION

(71) Applicant: SHISEIDO COMPANY, LTD., Tokyo (JP)

(72) Inventors: Ayano Matsuo, Yokohama (JP); Koichi Fujii, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/521,925

(22) PCT Filed: Aug. 31, 2015

(86) PCT No.: PCT/JP2015/074603
§ 371 (c)(1),
(2) Date: Apr. 26, 2017

(87) PCT Pub. No.: WO2016/067740
PCT Pub. Date: May 6, 2016

(65) Prior Publication Data
US 2017/0326060 A1    Nov. 16, 2017

(30) Foreign Application Priority Data
Oct. 31, 2014  (JP) ................................ 2014-223330

(51) Int. Cl.
| *A61K 8/87* | (2006.01) |
| *A61Q 1/04* | (2006.01) |
| *A61Q 1/10* | (2006.01) |
| *A61Q 1/14* | (2006.01) |
| *A61Q 5/06* | (2006.01) |
| *A61Q 19/00* | (2006.01) |
| *A61K 8/02* | (2006.01) |
| *A61K 8/06* | (2006.01) |
| *C08G 71/04* | (2006.01) |
| *A61K 8/90* | (2006.01) |

(52) U.S. Cl.
CPC ................ *A61K 8/87* (2013.01); *A61K 8/02* (2013.01); *A61K 8/06* (2013.01); *A61Q 1/04* (2013.01); *A61Q 1/10* (2013.01); *A61Q 1/14* (2013.01); *A61Q 5/06* (2013.01); *A61Q 19/00* (2013.01); *C08G 71/04* (2013.01); *A61K 8/90* (2013.01)

(58) Field of Classification Search
CPC ... A61K 8/87; A61K 8/90; A61K 8/06; A61K 8/02; C08G 71/04; A61Q 1/04; A61Q 19/00; A61Q 5/06; A61Q 1/14; A61Q 1/10
See application file for complete search history.

(56) References Cited

U.S. PATENT DOCUMENTS

| 2002/0098215 A1* | 7/2002 | Douin | ....................... | A61K 8/06 424/401 |
| 2010/0135938 A1* | 6/2010 | Ishikubo | ................ | A61K 8/062 424/59 |
| 2012/0164094 A1* | 6/2012 | Araki | ..................... | A61K 8/342 424/70.12 |
| 2013/0005835 A1* | 1/2013 | Uyama | .................. | A61K 8/062 514/784 |

FOREIGN PATENT DOCUMENTS

| EP | 2 565 233 | 3/2013 |
| EP | 2 796 126 | 10/2014 |
| JP | 11-501645 | 2/1999 |
| JP | 2000-63235 | 2/2000 |
| JP | 2001-226221 | 8/2001 |
| JP | 2005-139189 | 6/2005 |
| JP | 3828700 | 7/2006 |
| JP | 2006-190762 | 10/2006 |
| JP | 2007-291026 | 11/2007 |
| JP | 4979095 | 4/2012 |
| JP | 5035948 | 7/2012 |
| JP | 2013-82686 | 5/2013 |
| JP | 2014-122198 | 7/2014 |
| JP | 2014-122199 | 7/2014 |
| JP | A 2016-88868 | 5/2016 |

(Continued)

OTHER PUBLICATIONS

Certificate of Translation of and Translated English Granted Claims of Japanese Patent No. 6113695 dated Jul. 18, 2017, 2 pages—English.
JP 2014-223330, Decision to Grant a Patent dated Mar. 3, 2017, 3 pgs,—English, 3 pgs,—Japanese List of Documents issued from and filed to the JPO in the Examination of JP 2014-223330 1 pg.—English.
JP 2014-223330-, Notice of Reasons for Rejection dated Nov. 13, 2015, 6 pgs.—English, 5 pg.—Japanese.
JP 2014-223330, Notice of Reasons for Rejection dated Jun. 17, 2016, 8 pgs.—English, 6 pgs.—Japanese.
JP 2014-223330, Written Arguments dated Jan. 12, 2016, 8 pgs.—English; 5 pgs.—Japanese.

(Continued)

*Primary Examiner* — Rabon A Sergent
(74) *Attorney, Agent, or Firm* — Andrew F. Young, Esq.; Lackenbach Siegel, LLP

(57) ABSTRACT

The present invention provides an oil-in-water emulsion composition thickened with a hydrophobically modified polyether urethane, the composition having improved high-temperature stability and giving a pudding-like unique feeling. The invention provides an elastic jelly-like composition characterized in that a hydrophobically modified polyether urethane has been incorporated into an oil-in-water emulsion including oil droplets with an average particle diameter of 150 nm or smaller. The elastic jelly-like composition is transparent or translucent, gives a pudding-like elastic feeling, has excellent viscosity stability at high temperatures, and is suitable for use as a cosmetic-preparation base. The hydrophobically modified polyether urethane is especially preferably a PEG-240/decyltetradeceth-20/HDI copolymer.

4 Claims, 1 Drawing Sheet

(56) References Cited

FOREIGN PATENT DOCUMENTS

JP      B 6113695      4/2017
RU        2403271      1/2009

OTHER PUBLICATIONS

JP 2014-223330, Written Amenedment dated Jan. 12, 2016, 2 pgs.—English, 1 pg.—Japanese.
JP 2014-223330, Written Argument dated Oct. 7, 2016, 8 pgs—English 6 pgs.—Japanese.
JP 2014-223330, Written Amendment dated Oct. 7, 2016; 2 pgs.—English, 5 pgs.—Japanese.
PCT/JP2015/074603, International Search Report and Written Opinion, dated Nov. 17, 2015, 3 pages—English, 8 pages—Japanese.
RHEOLATE FX 1100, Elementis Specialties, 2010, www.elementis-specialties.com; 2 pages.
RU 2017116827/15, Russian Search Report dated Sep. 7, 2018, 2 pages—English, 2 pages—Russian.
RU 2017116827/15, Russian Office Action dated Sep. 18, 2018, 8 pages—English, 7 pages—Russian.
TW 10720472200, Taiwan Office Action, dated May 28, 2018, 5 pages—Englisih, 5 pages—Chinese.

* cited by examiner

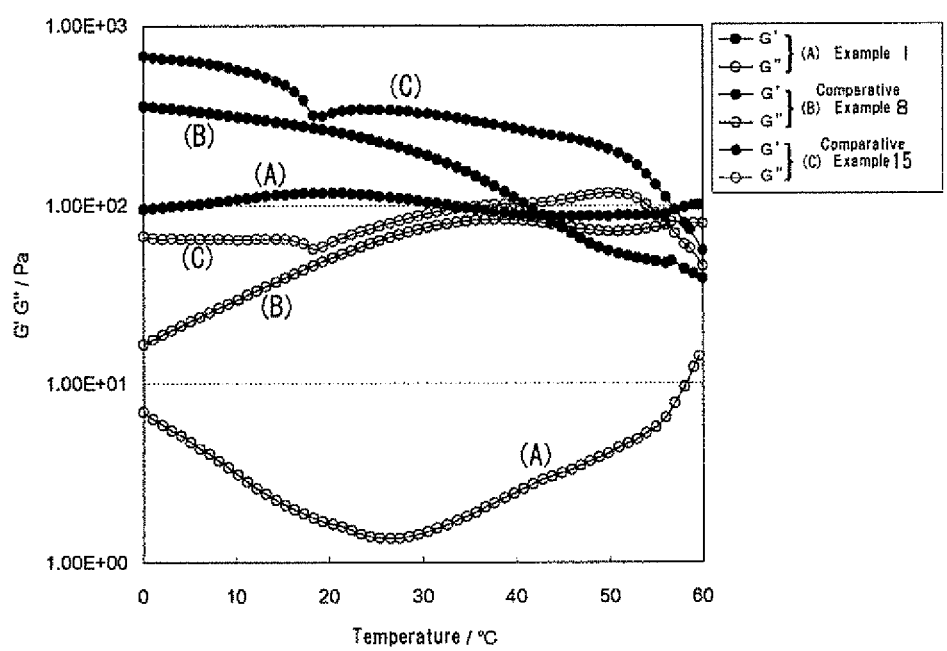

ELASTIC JELLY-LIKE COMPOSITION

CROSS REFERENCE TO RELATED APPLICATIONS

This application relates to and claims priority as a § 371 national phase, from PCT/JP2015/074603 FILED Aug. 31, 2015, the entire contents of which are incorporated herein by reference, which in turn claims priority from JP 2014-223330 filed Oct. 31, 2014.

TECHNICAL FIELD

The present invention relates to cosmetics having a unique texture. More specifically, the present invention relates to jelly-like oil-in-water emulsified cosmetics having unique jiggling elasticity as well as having excellent high-temperature stability.

BACKGROUND ART

Hydrophobically modified Ethoxylated Urethane Copolymers (HEUR) are blended as a water-soluble thickener having excellent viscosity stabilizing property and suitable texture in cosmetic compositions and the like (see, e.g., Patent Document 1). Compositions thickened with a hydrophobically modified ethoxylated urethane (also referred to as "hydrophobically modified polyether urethane") provide a unique jiggling touch and are attractive as cosmetic base compositions to be applied to skin and the like.

Such compositions are, however, characteristically difficult to cause change in the viscosity due to the concentration of a salt to be co-blended or pH variation of the compositions, but have a problem of reduction in the viscosity when stored at a high temperature (e.g., 50° C.). Patent Document 1 suggests that addition of a water-soluble polymer such as carboxyl vinyl polymers and xanthan gum in addition to hydrophobically modified ethoxylated urethane can prevent reduction in the viscosity at high temperatures.

Patent Documents 2 and 3 describe that a combination of hydrophobically modified ethoxylated urethane with a microgel of a thickener can provide a synergistic thickening effect. In Patent Document 2, a microgel obtained by grinding a gel formed from a hydrophilic compound having a gelling ability such as agar and gellan gum is blended. In Patent Document 3, a microgel obtained by dissolving water-soluble ethylenically unsaturated monomers (specifically, dimethylacrylamide and 2-acrylamido-2-methylpropane sulphonate) in a dispersed phase and radically polymerizing the monomers in the dispersed phase is blended.

However, in the case of co-blending the water-soluble polymer described in Patent Document 1 or the microgels of a thickener described in Patent Documents 2 and 3 in a composition containing hydrophobically modified ethoxylated urethane, improved high-temperature stability and a synergistic thickening effect can be obtained, but mixing a third component such as an oily component or an amphiphile may remove a jiggling unique feeling originally possessed by the composition thickened with the hydrophobically modified ethoxylated urethane.

PRIOR ART DOCUMENTS

Patent Documents

Patent Document 1: Japanese Patent No. 3828700
Patent Document 2: Japanese Patent No. 4979095
Patent Document 3: Japanese Patent No. 5035948

SUMMARY OF THE INVENTION

Problem to be Solved by the Invention

Accordingly, it is an object of the present invention to provide an elastic jelly composition that improves high-temperature stability of an oil-in-water emulsified composition thickened with a hydrophobically modified ethoxylated urethane with retaining its jiggling unique feeling.

Means for Solving the Problem

The present inventors have extensively studied to solve the problem described above and have found that blending hydrophobically modified ethoxylated urethane in an oil-in-water emulsified product having fine oil droplets of 150 nm or less can achieve a synergistic thickening effect even in the absence of other thickener as well as can improve the viscosity stability at high temperatures with the sense of use originally possessed by the hydrophobically modified ethoxylated urethane-containing composition (a texture having jiggling elasticity) maintained, having completed the present invention.

That is, the present invention provides an elastic jelly-like composition comprising an oil-in-water emulsified product having oil droplets having an average particle size of 150 nm or less and hydrophobically modified ethoxylated urethane contained in the oil-in-water emulsified product.

Advantageous Effects of the Invention

The composition of the present invention has a jiggling unique feeling caused by thickening with hydrophobically modified ethoxylated urethane, has little change in the viscosity due to external factors such as salt concentration, pH, and temperature, and can maintain stable viscosity especially at high temperatures.

The expressions "jiggling texture" and "jiggly feeling" in the present description mean a texture having unique elasticity as possessed by an aqueous solution of hydrophobically modified ethoxylated urethane (at a concentration of about 2% by mass or more). When a "composition having a jiggling texture" is pressed, for example, with a finger to place a load thereon, moderate resilience against the load is felt while the shape of the composition is deformed. When the finger is then released, the composition returns to its original shape and comes to rest after damping vibrations (provides a jiggling elasticity feeling). In contrast, when the load exceeds the limit, the shape considerably changes, and a touch as if the composition collapses at once is felt. This touch is similar to a "novel touch" described in Patent Document 3 above (paragraph [0022]). In Patent Document 3, however, a combination of hydrophobically modified ethoxylated urethane with a thickener microgel has provided a "novel touch", whereas, in the present invention, it is surprising that a low-viscous oil-in-water emulsified product, not a thickener, is combined to thereby achieve a synergistic thickening effect and a novel unique jiggling texture. Moreover, a fact that the novel touch in Patent Document 3 is lost in the presence of fine emulsified oil droplets has been found.

Incidentally, "a synergistic thickening effect" means an effect by which the viscosity increases exceeding the simple sum of the viscosity of a composition in which each ingredient is blended singly.

BRIEF DESCRIPTION OF DRAWINGS

FIG. 1 is a graph showing temperature changes in the storage modulus (G) and loss modulus (G") of the compositions of Example 1, Comparative Example 8, and Comparative Example 15.

DESCRIPTION OF EMBODIMENTS

The cosmetic composition of the present invention is characterized in that the composition comprising a hydrophobically modified ethoxylated urethane incorporated into an oil-in-water emulsified product having oil droplets having an average particle size of 150 nm or less.

The oil-in-water emulsified product having oil droplets having an average particle size of 150 nm or less is an emulsified composition in which oil droplets (a dispersed phase) dispersed in water (a continuous phase) have an average particle size of 150 nm or less. The average particle size of the oil droplets in the present description is considered the average value of the diameter of the oil droplets optically measured by the dynamic light scattering method or the like with an assumption that the particle shape of the oil droplets is spherical.

The average emulsified particle size in emulsified products (emulsions) generally used conventionally in cosmetics and the like is commonly one micrometer to about a few hundred micrometers. Emulsified products employed in the present invention are ultrafine emulsions having a nanometric average particle size. The average particle size is indispensably 150 nm or less, and can be preferably 140 nm or less, for example, 130 nm or less, 120 nm or less, 110 nm or less, 100 nm or less, 90 nm or less, 80 nm or less, or the like. In the case where the composition is to be transparent or translucent, its average particle size is preferably 100 nm or less. When the average particle size exceeds 150 nm, the viscoelastic behavior of the composition is altered, and the unique texture intended by the present invention cannot be achieved.

The lower limit of the average particle size is not particularly limited, and can be 5 nm or more, 10 nm or more, 20 nm or more, or 50 nm or more, for example. Naturally, the average particle size of the oil droplets in the emulsified product of the present invention can employ all the values between the upper value and the lower value described above. When the values are expressed in numerical ranges, all the numerical ranges such as 10 to 150 nm, 15 to 125 nm, and 20 to 100 nm are included.

An emulsified product having fine oil droplets having an average particle size of 150 nm or less (may be referred to as an "ultrafine emulsion") may be prepared by a method such as aggregation methods or dispersion methods.

The aggregation method is a colloid preparation method utilizing surface chemistry in which a homogeneously dissolved state is brought into a super saturated state by some means thereby to allow a component serving as a dispersed phase to appear. As specific approaches, HLB temperature emulsification, phase inversion emulsification, non-aqueous emulsification, D-phase emulsification, liquid crystal emulsification methods and the like are known.

The dispersion method is a method to finely pulverize aggregations in the dispersion phase by force. Specifically, the method is an emulsification method by use of the pulverizing force of an emulsifying apparatus.

Preferably used in the present invention is a dispersion method by high-pressure emulsification described in Japanese Patent No. 3398171. High-pressure emulsification is a method in which water-phase components and oil-phase components, pre-emulsified with a homomixer or the like as required, are subjected to high shear force by use of, for example, a high pressure homogenizer under a high pressure to thereby obtain an emulsified product having finer emulsified particles.

In the oil droplets in the emulsified product of the present invention (the oily phase or dispersed phase), at least an oil component and a surfactant are contained.

The oil component may be any of liquid oil components, solid oil components, or semisolid oil components. Examples of the oil component include liquid oils such as avocado oil, tsubaki oil, turtle oil, macadamia nut oil, corn oil, mink oil, olive oil, rape seed oil, yolk oil, sesame oil, persic oil, wheat germ oil, sazanque oil, castor oil, linseed oil, safflower oil, cottonseed oil, evening primrose oil, perilia oil, soybean oil, peanut oil, teaseed oil, kaya oil, rice bran oil, Chinese *paulownia* oil, Japanese *paulownia* oil, jojoba oil, germ oil, triglycerin, glycerin trioctanoate, glycerin triisopalmitate, and hydrogenated polydecene, solid oils such as cocoa butter, coconut oil, horse tallow, hydrogenated coconut oil, palm oil, beef tallow, mutton tallow, hydrogenated beef tallow, palm kernel oil, pork tallow, beef bone tallow, Japan wax, kernel oil, hydrogenated oil, neat's-foot oil, Japan wax, and hydrogenated castor oil, waxes such as bees wax, candelilla wax, cotton wax, carnauba wax, bayberry wax, Chinese wax, spermaceti wax, montan wax, rice bran wax, lanolin, kapok oil, lanolin acetate, liquid lanolin, sugarcane wax, lanolin fatty acid isopropyl, hexyl laurate, reduced lanolin, jojoba wax, hydrogenated lanolin, shellac wax, POE lanolin alcohol ether, POE lanolin alcoholacetate, lanolin fatty acid polyethylene glycol, and POE hydrogenated lanolin alcohol ether, hydrocarbons such as liquid paraffin, ozocerite, squalene, pristane, paraffin, ceresin, squalene, vaseline, and microcrystalline wax, synthetic esters such as isopropyl myristate, cetyl octoate, octyldodecyl myristate, isopropyl palmitate, butyl stearate, hexyl laurate, myristyl myristate, decyl oleate, hexyldecyl dimethyloctoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprate, diisostearyl malate, glycerin di-2-heptylundecandate, trimethylolpropane tri-2-ethylhexylate, trimethylolpropane triisostearate, pentaerythritol tetra-2-ethylhexylate, glycerin tri-2-ethylhexylate, trimethylolpropane triisostearate, cetyl-2-ethylhexanoate, 2-ethylhexyl palmitate, glycerin trimyristearate, glyceride tri-2-undecandate, castor oil fatty acid methyl ester, oil oleate, cetostearyl alcohol, acetoglyceride, 2-heptylundecyl palmitate, diisopropyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, and triethyl citrate, silicone oils such as dimethyl polysiloxane and methylphenyl polysiloxane, perfluorocarbons or perfluoropolyethers such as perfluorodecalin, perfluorohexane, and triperfluoro-n-butylamine, vitamins such as vitamin A and derivatives thereof, vitamin D and derivatives thereof, vitamin E and derivatives thereof, and vitamin K and derivatives thereof, sterols, and natural and synthetic perfumes.

The amount of the oil component blended in the composition of the present invention is preferably 0.5% by mass or more, more preferably 1% by mass or more, for example, 1.2% by mass or more, 1.5% by mass or more, or 2% by mass or more based on the total amount of the composition. The upper limit of the amount of the oil component blended is not particularly limited and is usually 25% by mass or less, for example, preferably 20% by mass or less. The upper limit is most preferably 1 to 20% by mass.

As the surfactant, anionic, cationic, or amphoteric ionic surfactants, or nonionic surfactants can be used, and such surfactants are not particularly limited.

For example, in the case of the above microemulsion prepared by high pressure emulsification, oil droplets comprise an amphiphile and a surfactant selected from those capable of forming a gel in an amphiphile-surfactant-water system at normal temperature or higher, and an oil, and microemulsions in which the substantially total amount of the amphiphile and surfactant is present at the interface of the oil droplets are particularly preferred. The gel is preferably the α-type from the viewpoint of stability, and the transition temperature of the gel is preferably 60° C. or more. As the amphiphile, higher alcohols and/or higher fatty acids having a carbon chain length of 16 or more are preferred. Specific examples include higher fatty acids such as lauric acid, myristic acid, palmitic acid, stearic acid, behenic acid (behenyl) acid, oleic acid, 12-hydroxystearic acid, undecylenic acid, tall oil acid, lanolin fatty acid, isostearic acid, linoleic acid, linolenic acid, and eicosapentaenoic acid, and linear/branched higher alcohols such as lauryl alcohol, cetyl alcohol, stearyl alcohol, behenyl alcohol, myristyl alcohol, oleyl alcohol, cetostearyl alcohol, monostearyl glycerine ether (batyl alcohol), 2-decyltetradecanol, lanolin alcohol, cholesterol, hexyldodecanol, isostearyl alcohol, and octyldodecanol. Additionally, as the surfactant, anionic or cationic ionic surfactants are preferred. Preferred examples of amphiphile-surfactant combinations include, but not limited to, behenic acid and/or behenyl alcohol (amphiphile)-behenic acid/potassium hydroxide fatty acid soap (surfactant), stearic acid and/or stearyl alcohol (amphiphile)-stearic acid/potassium hydroxide fatty acid soap (surfactant), stearyl alcohol (amphiphile)-sodium cetyl sulfate (surfactant), and behenyl alcohol (amphiphile)-behenyltrimethyl ammonium chloride (surfactant) and behenyl alcohol (amphiphile)-stearyltrimethyl ammonium chloride (surfactant).

Furthermore, the total amount of the amphiphile and the surfactant blended is preferably 0.2% by mass or more based on the aqueous phase, and the amount of the oil component to the total amount of the amphiphile and the surfactant blended is preferably ½ or more, more preferably 1/1 or more.

In the present invention, as the hydrophobically modified ethoxylated urethane to be blended to the oil-in-water emulsified product described above, one represented by the following formula (I):

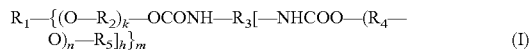

is preferably used.

In the above formula (I), $R_1$, $R_2$, and $R_4$ each independently represent a hydrocarbon group having 2 to 4 carbon atoms. The group is preferably an alkyl group or an alkylene group having 2 to 4 carbon atoms.

$R_3$ represents a hydrocarbon group having 1 to 10 carbon atoms, which may have a urethane bond.

$R_5$ represents a hydrocarbon group having 8 to 36, preferably 12 to 24 carbon atoms.

m is a number of 2 or more, preferably 2. h is a number of 1 or more, preferably 1. k is a number of 1 to 500, preferably a number of 100 to 300. n is a number of 1 to 200, preferably a number of 10 to 100.

The hydrophobically modified ethoxylated urethane represented by the above formula (I) can be obtained by reacting one or two or more polyetherpolyols represented by, for example, $R_1$—[(O—$R_2$)$_k$—OH]$_m$ (wherein $R_1$, $R_2$, K and m are as defined above), one or two or more polyisocyanates represented by $R_3$—(NCO)$_{h+1}$ (wherein $R_3$ and h are as defined above), and one or two or more polyether monoalcohols represented by HO—($R_4$—O)$_n$—$R_5$ (wherein $R_4$, $R_5$, and n are as defined above).

In this production method, $R_1$ to $R_5$ in the formula (I) are determined by $R_1$—[(O—$R_2$)$_k$—OH]$_m$, $R_3$—(NCO)$_{h+1}$, and HO—($R_4$—O)$_n$—$R_5$, which are the raw materials. The feed ratio of the above three is not particularly limited, and the ratio of the isocyanate group derived from the polyisocyanate to the hydroxyl group derived from the polyetherpolyol and polyether monoalcohol is preferably NCO/OH=0.8:1 to 1.4:1.

The polyetherpolyol compound represented by the above formula $R_1$—[(O—$R_2$)$_k$—OH]$_m$ can be produced by addition-polymerizing an alkylene oxide or a styrene oxide, such as ethylene oxide, propylene oxide, butylene oxide, and epichlorohydrin to an m-hydric polyol.

Here the polyol is preferably a dihydric to octahydric one, and examples include dihydric alcohols such as ethylene glycol, propylene glycol, butylene glycol, hexamethylene glycol, and neopentyl glycol; trihydric alcohols such as glycerin, trioxyisobutane, 1,2,3-butanetriol, 1,2,3-pentatriol, 2-methyl-1,2,3-propanetriol, 2-methyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-pentanetriol, pentamethylglycerin, pentaglycerin, 1,2,4-butanetriol, 1,2,4-pentanetriol, trimethylolethane, and trimethylolpropane; tetrahydric alcohols such as pentaerythritol, 1,2,3,4-pentanetetrol, 2,3,4,5-hexanetetrol, 1,2,4,5-pentanetetrol, and 1,3,4,5-hexanetetrol; pentahydric alcohols such as adonitol, arabitol, and xylitol; hexahydric alcohols such as dipentaerythritol, sorbitol, mannitol, and iditol; and octahydric alcohols such as sucrose.

$R_2$ is determined by the alkylene oxide, styrene oxide or the like to be added. Especially for being readily available and for exhibiting the excellent effect, preferred are alkylene oxides having from 2 to 4 carbon atoms or styrene oxide.

The alkylene oxide, styrene oxide or the like to be added may be in the form of homopolymerization or of random polymerization or block polymerization of two or more different types thereof. The addition method may be any ordinary one. The degree of polymerization k is from 1 to 500. The proportion of the ethylene group that occupies $R_2$'s is preferably 50 to 100% by mass of all the $R_2$'s.

The molecular weight of $R_1$—[(O—$R_2$)$_k$—OH]$_m$ is preferably 500 to 100,000, more preferably 1,000 to 50,000.

The polyisocyanate represented by the above formula $R_3$—(NCO)$_{h+1}$ is not particularly limited as long as it has at least two isocyanate groups in the molecule. Examples include aliphatic diisocyanates, aromatic diisocyanates, alicyclic diisocyanates, biphenyl diisocyanates, and phenylmethane di-, tri- and tetra-isocyanates.

Examples of the aliphatic diisocyanate include methylene diisocyanate, dimethylene diisocyanate, trimethylene diisocyanate, tetramethylene diisocyanate, pentamethylene diisocyanate, hexamethylene diisocyanate, dipropylether diisocyanate, 2,2-dimethylpentane diisocyanate, 3-methoxyhexane diisocyanate, octamethylene diisocyanate, 2,2,4-trimethylpentane diisocyanate, nonamethylene diisocyanate, decamethylene diisocyanate, 3-butoxyhexane diisocyanate, 1,4-butylene glycol dipropyl ether diisocyanate, thiodihexyl diisocyanate, metaxylylene diisocyanate, paraxylylene diisocyanate, and tetramethylxylylene diisocyanate.

Examples of the aromatic diisocyanate include metaphenylene diisocyanate, paraphenylene diisocyanate, 2,4-tolylene diisocyanate, 2,6-tolylene diisocyanate, dimethylbenzene diisocyanate, ethylbenzene diisocyanate, isopropylbenzene diisocyanate, tolidinediisocyanate, 1,4-naphthalene diisocyanate, 1,5-naphthalene diisocyanate, 2,6-naphthalene diisocyanate, and 2,7-naphthalene diisocyanate.

Examples of the alicyclic diisocyanate include hydrogenated xylylene diisocyanate and isophorone diisocyanate.

Examples of the biphenyl diisocyanate include biphenyl diisocyanate, 3,3'-dimethylbiphenyl diisocyanate, and 3,3'-dimethoxybiphenyl diisocyanate.

Examples of the phenylmethane diisocyanate include diphenylmethane-4,4'-diisocyanate, 2,2'-dimethyldiphenylmethane-4,4'-diisocyanate, diphenyldimethylmethane-4,4'-diisocyanate, 2,5,2',5'-tetramethyldiphenylmethane-4,4'-diisocyanate, cyclohexyl bis(4-isocyanatophenyl)methane, 3,3'-dimethoxydiphenylmethane-4,4'-diisocyanate, 4,4'-dimethoxydiphenylmethane-3,3'-diisocyanate, 4,4'-diethoxydiphenylmethane-3,3'-diisocyanate, 2,2'-dimethyl-5,5'-dimethoxydiphenylmethane-4,4'-diisocyanate, 3,3'-dichlorodiphenyldimethylmethane-4,4'-diisocyanate, and benzophenone-3,3'-diisocyanate.

Examples of the phenylmethane triisocyanate include 1-methylbenzene-2,4,6-triisocyanate, 1,3,5-trimethylbenzene-2,4,6-triisocyanate, 1,3,7-naphthalene triisocyanate, biphenyl-2,4,4'-triisocyanate, diphenylmethane-2,4,4'-triisocyanate, 3-methyldiphenylmethane-4,6,4'-triisocyanate, triphenylmethane-4,4',4"-triisocyanate, 1,6,11-undecane triisocyanate, 1,8-diisocyanate-4-isocyanatemethyloctane, 1,3,6-hexamethylene triisocyanate, bicycloheptane triisocyanate, and tris(isocyanatophenyl) thiophosphate.

These polyisocyanate compounds also may be used in the form of a dimer or a trimer (isocyanurate bond) and also may be reacted with an amine to be used as biuret.

Also usable are polyisocyanates having a urethane bond, which are prepared by reacting these polyisocyanate compounds with polyols. As the polyols, dihydric to octahydric ones are preferred. The aforementioned polyols are preferred. In the case where a trihydric or more polyisocyanate is used as $R_3—(NCO)_{h+1}$, these polyisocyanates having a urethane bond are preferred.

The polyether monoalcohol represented by the above formula $HO—(R_4—O)_n—R_5$ is not particularly limited as long as the polyether monoalcohol is a monohydric alcohol polyether. Such compounds can be obtained by addition-polymerizing an alkylene oxide or a styrene oxide, such as ethylene oxide, propylene oxide, butylene oxide, and epichlorohydrin to a monohydric alcohol.

The monohydric alcohol as referred to herein is one represented by the following formula (II), (III), or (IV):

(II)

(III)

(IV)

That is, $R_5$ is a group obtained by removing the hydroxyl group from the monohydric alcohol of the above formulas (II) to (IV). In the above formulas (II) to (IV), $R_6$, $R_7$, $R_8$, $R_{10}$, and $R_{11}$ each represent a hydrocarbon group, for example, an alkyl group, an alkenyl group, an alkylaryl group, a cycloalkyl group, and a cycloalkenyl group.

Examples of the alkyl group includes methyl, ethyl, propyl, isopropyl, butyl, isobutyl, tertiary butyl, pentyl, isopentyl, neopentyl, tertiary pentyl, hexyl, heptyl, octyl, 2-ethylhexyl, nonyl, decyl, undecyl, dodecyl, tridecyl, isotridecyl, myristyl, palmityl, stearyl, isostearyl, icosyl, docosyl, tetracosyl, triacontyl, 2-octyldodecyl, 2-dodecylhexadecyl, 2-tetradecyloctadecyl, and monomethyl-branched isostearyl.

Examples of the alkenyl group includes vinyl, allyl, propenyl, isopropenyl, butenyl, pentenyl, isopentenyl, hexenyl, heptenyl, octenyl, nonenyl, decenyl, undecenyl, dodecenyl, tetradecenyl, and oleyl.

Examples of the alkylaryl group includes phenyl, toluyl, xylyl, cumenyl, mesityl, benzyl, phenethyl, styryl, cinnamyl, benzhydryl, trityl, ethylphenyl, propylphenyl, butylphenyl, pentylphenyl, hexylphenyl, heptylphenyl, octylphenyl, nonylphenyl, α-naphthyl, and β-naphthyl.

Examples of the cycloalkyl group and the cycloalkenyl group include cyclopentyl, cyclohexyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl.

In the above formula (III), $R_9$ represents a hydrocarbon group, for example, an alkylene group, an alkenylene group, an alkylarylene group, a cycloalkylene group, and a cycloalkenylene group.

$R_5$ represents a hydrocarbon group and is preferably an alkyl group among others. Furthermore, the total number of the carbon atoms in the group is 8 to 36, particularly preferably 12 to 24.

The alkylene oxide, styrene oxide or the like to be added may be in the form of homopolymerization or of random polymerization or block polymerization of two or more different types thereof. The addition method may be any ordinary one. The degree of polymerization n is 0 to 1000, preferably 1 to 200, more preferably 10 to 200. Also, the proportion of the ethylene group that occupies $R_4$'s is preferably 50 to 100% by weight of all the $R_4$'s, more preferably 65 to 100% by weight.

The copolymer represented by the formula (I) can be produced in the same manner as that for ordinary reaction of polyether and isocyanate, for example, by reaction under heating at 80 to 90° C. for 1 to 3 hours.

In reacting the polyether polyol (A) represented by $R_1—[(O—R_2)_k—OH]_m$, the polyisocyanate (B) represented by $R_3—(NCO)_{h+1}$, and the polyether monoalcohol (C) represented by $HO—(R_4—O)_n—R_5$, products other than the copolymer having the structure of the formula (I) may be generated as side products. For example, in the case where a diisocyanate is used, the main product is the C-B-A-B-C type copolymer represented by the formula (I), and in addition thereto, other copolymers such as C-B-C type one, C-B-(A-B)$_x$-A-B-C type one and the like may be generated as side products. In this case, without particularly separating the copolymer of the formula (I) type, a mixture that contains the copolymer of the formula (I) type may be used in the invention.

A particularly preferred example is hydrophobically modified ethoxylated urethane of which INCI name is "(PEG-240/decyltetradeceth-20/HDI) copolymer (PEG-240/HDI COPOLYMER BISDECYLTETRADECETH-20 ETHER)". The copolymer is commercially available from ADEKA CORPORATION under the product name "Adekanol GT-700".

The amount of the hydrophobically modified ethoxylated urethane blended in the compositions of the present invention is 0.1% by mass or more, preferably 0.3% by mass or more, more preferably 0.5% by mass or more based on the total amount of the composition. The upper limit of the amount blended is 10% by mass or less, preferably 6% by mass or less, more preferably 4% by mass or less based on the total amount of the composition. The amount blended is most preferably in the range of 0.1 to 4% by mass. When the amount blended is less than 0.1% by mass or exceeds 10% by mass, the intended unique texture may not be achieved.

The elastic jelly-like composition of the present invention can be prepared by preparing an oil-in-water emulsified product having oil droplets having an average particle size of 150 nm or less (ultrafine emulsion), diluting the emulsified product with an aqueous medium as required, and then thickening the emulsified product by addition of a hydrophobically modified ethoxylated urethane solution which has been dissolved in an aqueous medium of quantum sufficit thereto.

The elastic jelly-like composition of the present invention is preferably transparent or translucent depending on the application. The composition is a thickened aqueous composition having a unique jiggling texture as described above. When a load exceeding the limit is applied, the composition collapses at once and provides a fresh touch as if water is sprung out therefrom. Accordingly, the elastic jelly-like composition of the present invention is particularly suitable for use as cosmetic bases to be applied to skin and the like.

A cosmetic containing the elastic jelly-like composition of the present invention as its base is prepared by blending various ingredients for the production of the cosmetic to the elastic jelly-like composition. Such various ingredients are blended in the aqueous phase (continuous phase) or in the oily phase (dispersed phase) of the oil-in-water emulsified product depending on their properties.

Examples of the various ingredients include additive ingredients that may be usually blended in cosmetics, for example, lower alcohols such as ethanol, polyhydric alcohols, various extracts, moisturizers, antioxidants, buffers, preservative, dyes, fragrances, chelators, and pH adjusting agents. These may be blended depending on the application and purpose of the cosmetics.

Needless to say, the various ingredients described above should be blended within a range not impairing the effect of the present invention. For example, the water-soluble polymer described in Patent Document 1 and the thickener microgels described in Patent Documents 2 and 3 also can be blended within a range not impairing the jiggling texture, which is the effect of the present invention (for example, preferably in the amount of less than 0.2% by mass, most preferably in the amount of less than 0.1% by mass). In contrast, the present invention includes aspects of a transparent or translucent composition not containing the water-soluble polymer or the thickener microgel.

Specific examples of the cosmetic include skin care cosmetics such as moisturizing gels, massage gels, essences, skin lotions, and milky lotions, makeup cosmetics, suncare products, hair cosmetics such as hair setting agents and hair gels, and hair dyes.

Examples

The present invention will be described more specifically by referring to examples below, but the scope of the present invention is not restricted by these examples. Unless otherwise specified, the amount blended is expressed in % by mass based on the total amount. The hydrophobically modified ethoxylated urethane used in the following examples and comparative examples is "Adekanol GT-700 (manufactured by ADEKA CORPORATION)".

Compositions having the formulation in the following Tables 1 to 6 (Examples and Comparative Examples) were evaluated for "appearance", "jiggly feeling", "emulsified particle size", "viscosity", and "thickening properties at 50° C.". The evaluation method and evaluation criteria for each evaluation points are as follows.

<Appearance>

The composition of each example was visually observed and classified into "transparent", "translucent", "slightly whitely turbid", or "whitely turbid".

<Jiggly Feeling>

Specialized panelists (10 females) were asked to use the composition of each example and evaluate the composition for its jiggling unique touch based on the following evaluation criteria.

(Evaluation Criteria)

A: Nine or more panelists replied, "The composition has a jiggling unique texture".

B: Seven to eight panelists replied, "The composition has a jiggling unique texture".

C: Five to six panelists replied, "The composition has a jiggling unique texture".

D: Three to four panelists replied, "The composition has a jiggling unique texture".

E: Two or less panelists replied, "The composition has a jiggling unique texture".

<Emulsified Particle Size>

The emulsified particle size was measured with a Zeta sizer nano (manufactured by Malvern Instruments Ltd.). The measurement was conducted at 25° C.

<Viscosity Measurement>

For viscosity measurement, data used were those obtained by measuring by use of a Reometer MCR300 (manufactured by Anton Paar GmbH) under conditions of shear speeds 1 $s^{-1}$ and 10 $s^{-1}$ for one minute. The measurement was conducted at 25° C.

For the thickening properties at 50° C., the temperature dependency of the dynamic viscoelastic behavior under a 1% strain of the composition of each example was measured (10° C. to 60° C., 1° C./min), and the tan δ value at 50° C. was evaluated as follows.

A: tan δ<0.4
B: 0.4≤tan δ<0.6
C: 0.6≤tan δ<0.8
D: 0.8≤tan δ<1
E: 1≤tan δ

TABLE 1

|  | Comparative Example 1 | Comparative Example 2 | Example 1 | Comparative Example 3 | Comparative Example 4 | Comparative Example 5 | Comparative Example 6 | Comparative Example 7 |
|---|---|---|---|---|---|---|---|---|
| 1) Ion exchanged water | 19.2 | — | 19.2 | 19.2 | 19.2 | 19.2 | 19.2 | 19.2 |
| 2) Sodium stearoyl glutamate | 0.6 | — | 0.6 | 0.6 | 0.6 | 0.6 | 0.6 | 0.6 |
| 3) Dipropylene glycol | 3 | — | 3 | 3 | 3 | 3 | 3 | 3 |

TABLE 1-continued

|  | Comparative Example 1 | Comparative Example 2 | Example 1 | Comparative Example 3 | Comparative Example 4 | Comparative Example 5 | Comparative Example 6 | Comparative Example 7 |
|---|---|---|---|---|---|---|---|---|
| 4) Glycerin | 1.2 | — | 1.2 | 1.2 | 1.2 | 1.2 | 1.2 | 1.2 |
| 5) Behenyl alcohol | 1 | — | 1 | 1 | 1 | 1 | 1 | 1 |
| 6) Stearyl alcohol | 1 | — | 1 | 1 | 1 | 1 | 1 | 1 |
| 7) Hydrogenated polydecene | 4 | — | 4 | 4 | 4 | 4 | 4 | 4 |
| 8) Hydrophobically modified ethoxylated urethane | — | 1 | 1 | 1 | — | — | — | — |
| 9) Carboxyvinyl polymer | — | — | — | — | 0.3 | — | — | — |
| 10) (Dimethylacrylamide/sodium acryloyldimethyltaurate) crosspolymer | — | — | — | 0.2 | — | 0.5 | — | — |
| 11) Succinoglycan | — | — | — | — | — | — | 0.25 | — |
| 12) High-molecular weight polyethylene glycol | — | — | — | — | — | — | — | 0.1 |
| 13) Potassium hydroxide | — | — | — | — | 0.01 | — | — | — |
| 14) Ion exchanged water | Quantum sufficit | Quantum sufficit | Quantum sufficit | Quantum sufficit | Quantum sufficit | Quantum sufficit | Quantum sufficit | Quantum sufficit |
| 15) Dipropylene glycol | 4 | — | 4 | 4 | 4 | 4 | 4 | 4 |
| 16) Glycerin | 1.8 | — | 1.8 | 1.8 | 1.8 | 1.8 | 1.8 | 1.8 |
| 17) Ion exchanged water |  | Balance |  |  |  |  |  |  |
| Total | 100 | 100 | 100 | 100 | 100 | 100 | 100 | 100 |
| Appearance | Translucent | Transparent | Translucent | Whitely turbid | Whitely turbid | Whitely turbid | Whitely turbid | Whitely turbid |
| Jiggly feeling | E | C | A | C | E | E | E | E |
| Emulsified particle size/nm | 53.3 | — | 53.3 | 57.2 | 53.3 | 53.3 | 53.3 | 53.3 |
| Viscosity cp 1 $s^{-1}$/Pa·s | 0.0091 | 5.14 | 39.7 | 62.9 | 3.32 | 2.39 | 1.79 | 0.012 |
| Viscosity cp 10 $s^{-1}$/Pa·s | 0.0060 | 1.31 | 6.97 | 11.4 | 9.949 | 1.26 | 0.27 | 0.0088 |
| Thickening properties at 50° C. | E | E | A | A | E | E | E | E |

Production Method:

A mixture prepared by mixing and dissolving 5) to 7) under stirring and heating at 80° C. was mixed under stirring into a product prepared by dissolving 1) to 4) under heating at 75° C., and the resulting mixture was high-pressure emulsified under a pressure of about 100 MPa (as the high-pressure emulsifying apparatus, a Nanomizer mark II (manufactured by YOSHIDA KIKAI CO., LTD.) and an H-20 type Homogenizer (manufactured by SANWA ENGINEERING CO., LTD.) were used).

In Comparative Example 1, the high-pressure emulsified product was diluted with a mixture of 14) to 16).

In Comparative Example 2, the hydrophobically modified ethoxylated urethane was dissolved in water and used as an aqueous solution.

In Example 1, Comparative Example 3, and Comparative Examples 5 to 7, the high-pressure emulsified product was diluted with a constant amount of a mixture of 15) to 17) and then thickened with the hydrophobically modified ethoxylated urethane or an aqueous solution of each thickener.

In Comparative Example 4, the high-pressure emulsified product was diluted with a constant amount of a mixture of 15) to 17) and then thickened with a mixture prepared by neutralizing 9) with 13).

As is clearly seen from Table 1, Comparative Example 1, which is an oil-in-water emulsified product having an average particle size of 150 nm or less and does not contain the hydrophobically modified ethoxylated urethane or other thickener, has a very low viscosity and provides no jiggling texture. Comparative Example 2, which is a 1% by mass aqueous solution of the hydrophobically modified ethoxylated urethane, has a certain degree of viscosity and provides a jiggling texture but has a significant reduction in the viscosity at 50° C. In contrast to these, the composition of Example 1, which was prepared by thickening the oil-in-water emulsified product having an average particle size of 150 nm or less with 1% by mass of the hydrophobically modified ethoxylated urethane, had a synergistically increased viscosity compared to those of Comparative Examples 1 and 2, provided a jiggling texture as well as exhibited no reduction in the viscosity at 50° C. However, in Comparative Examples 3 to 7, in which all or a portion of the hydrophobically modified ethoxylated urethane of Example 1 was replaced by other thickener, the appearance transparency was reduced and furthermore, a sufficient viscosity was not achieved to thereby cause the jiggly feeling to be lost. Moreover, in many cases, reduction in the viscosity at 50° C. was confirmed.

TABLE 2

|  | Comparative Example 2 | Comparative Example 8 | Example 9 | Comparative Example 10 | Comparative Example 11 | Comparative Example 12 | Comparative Example 3 | Comparative Example 13 | Comparative Example 14 |
|---|---|---|---|---|---|---|---|---|---|
| 1) Ion exchanged water | — | — | — | — | — | — | 19.2 | — | — |
| 2) Sodium stearoyl glutamate | — | — | — | — | — | — | 0.6 | — | — |
| 3) Dipropylene glycol | — | — | — | — | — | — | 3 | — | — |
| 4) Glycerin | — | — | — | — | — | — | 1.2 | — | — |
| 5) Behenyl alcohol | — | — | — | — | — | — | 1 | — | — |
| 6) Stearyl alcohol | — | — | — | — | — | — | 1 | — | — |
| 7) Hydrogenated polydecene | — | — | — | — | — | — | 4 | — | — |

TABLE 2-continued

| | Comparative Example 2 | Comparative Example 8 | Example 9 | Comparative Example 10 | Comparative Example 11 | Comparative Example 12 | Comparative Example 3 | Comparative Example 13 | Comparative Example 14 |
|---|---|---|---|---|---|---|---|---|---|
| 8) Hydrophobically modified ethoxylated urethane | 1 | 2 | 1 | 1 | 1 | 1 | 1 | 1 | 1 |
| 9) Carboxyvinyl polymer | — | — | 0.1 | 0.3 | — | — | — | — | — |
| 10) (Dimethylacrylamide/sodium acryloyldimethyltaurate) crosspolymer | — | — | — | — | 0.3 | 0.5 | 0.2 | — | — |
| 11) Succinoglycan | — | — | — | — | — | — | — | 0.3 | 0.5 |
| 12) High-molecular weight polyethylene glycol | — | — | — | — | — | — | — | — | — |
| 13) Potassium hydroxide | — | — | 0.03 | 0.1 | — | — | — | — | — |
| 14) ion exchanged water | Quantum sufficit | Quantum sufficit | Quantum sufficit | Quantum sufficit | Quantum sufficit | Quantum sufficit | Quantum sufficit | Quantum sufficit | Quantum sufficit |
| 15) Dipropylene glycol | — | — | — | — | — | — | 4 | — | — |
| 16) Glycerin | — | — | — | — | — | — | 1.8 | — | — |
| 17) ion exchanged water | Balance | Balance | Balance | Balance | Balance | Balance | Balance | Balance | Balance |
| Total | 100 | 100 | 100 | 100 | 100 | 100 | 100 | 100 | 100 |
| Appearance | Transparent | Transparent | Transparent | Transparent | Transparent | Transparent | Whitely turbid | Translucent | Translucent |
| Jiggly feeling | C | A | C | C | A | A | C | D | D |
| Emulsified particle size/nm | — | — | — | — | — | — | 57.2 | — | — |
| Viscosity cp 1 s$^{-1}$/Pa · s | 5.14 | 49.7 | 52.9 | 75.2 | 149 | 227 | 62.9 | 9.66 | 13.9 |
| Viscosity cp 10 s$^{-1}$/Pa · s | 1.31 | 8.31 | 8.98 | 12.2 | 35.2 | 45.3 | 11.4 | 0.978 | 1.40 |
| Thickening properties at 50° C. | E | E | A | A | A | A | A | A | A |

In the results shown in Table 2, when the amount added of the hydrophobically modified ethoxylated urethane aqueous solution was increased to 2% by mass, a jiggly feeling can be obtained, but reduction in the viscosity at 50° C. is observed (Comparative Example 8). As suggested in Patent Documents 1 to 3, blending a water-soluble polymer such as a carboxyvinyl polymer and a thickener microgel can prevent reduction in the viscosity at 50° C. However, when only a water-soluble polymer is added, a jiggly feeling cannot be obtained (Comparative Examples 9 to 10, 13 to 14). When a thickener microgel is added, a jiggly feeling can be obtained, but in a system in which emulsified particles coexist, such a jiggly feeling becomes impaired (Comparative Examples 11, 12, and 3).

TABLE 3

| | Comparative Example 1 | Comparative Example 2 | Comparative Example 8 | Example 1 | Example 2 | Example 3 | Example 4 | Comparative Example 15 |
|---|---|---|---|---|---|---|---|---|
| 1) Ion exchanged water | 19.2 | — | — | 19.2 | 19.2 | 19.2 | 19.2 | 19.2 |
| 2) Sodium stearoyl glutamate | 0.6 | — | — | 0.6 | 0.6 | 0.6 | 0.6 | 0.6 |
| 3) Dipropylene glycol | 3 | — | — | 3 | 3 | 3 | 3 | 3 |
| 4) Glycerin | 1.2 | — | — | 1.2 | 1.2 | 1.2 | 1.2 | 1.2 |
| 5) Behenyl alcohol | 1 | — | — | 1 | 1 | 1 | 1 | 1 |
| 6) Stearyl alcohol | 1 | — | — | 1 | 1 | 1 | 1 | 1 |
| 7) Hydrogenated polydecene | 4 | — | — | 4 | 4 | 4 | 4 | 4 |
| 8) Hydrophobically modified ethoxylated urethane | — | 1 | 2 | 1 | 1 | 1 | 1 | 1 |
| 9) Ion exchanged water | Quantum sufficit | Quantum sufficit | Quantum sufficit | Quantum sufficit | Quantum sufficit | Quantum sufficit | Quantum sufficit | Quantum sufficit |
| 10) Dipropylene glycol | 4 | — | — | 4 | 4 | 4 | 4 | 4 |

TABLE 3-continued

|  | Comparative Example 1 | Comparative Example 2 | Comparative Example 8 | Example 1 | Example 2 | Example 3 | Example 4 | Comparative Example 15 |
|---|---|---|---|---|---|---|---|---|
| 11) Glycerin | 1.8 | — | — | 1.8 | 1.8 | 1.8 | 1.8 | 1.8 |
| 12) Ion exchanged water | Balance | Balance | Balance | Balance | Balance | Balance | Balance | Balance |
| Total | 100 | 100 | 100 | 100 | 100 | 100 | 100 | 100 |
| Appearance | Translucent | Transparent | Transparent | Translucent | Translucent | Slightly whitely turbid | Whitely turbid | Whitely turbid |
| Jiggly feeling | E | C | A | A | A | A | A | E |
| Emulsified particle size/nm | 53.3 | — | — | 53.3 | 63.2 | 81 | 145 | ~2500 |
| Viscosity cp 1 s$^{-1}$/Pa · s | 0.0091 | 5.14 | 49.7 | 39.7 | 43.2 | 23.0 | 4.92 | 21.1 |
| Viscosity cp 10 s$^{-1}$/Pa · s | 0.0060 | 1.31 | 8.31 | 6.97 | 6.01 | 7.40 | 0.949 | 3.96 |
| Thickening properties at 50° C. | E | E | E | A | A | A | B | B |

Production Method:

Examples 2 to 4 were prepared in the same manner as in Example 1. However, the number of times of high-pressure emulsification was changed to vary the particle size.

In Comparative Example 15, a mixture prepared by dissolving 5) to 7) under heating at 80° C. was mixed under stirring into a product prepared by dissolving 1) to 4) under heating at 75° C. The resulting mixture was treated with a homomixer at 9000 rpm for one minute and then quenched. A mixture of 8) to 12) was added thereto.

From the results shown in Table 3, when the oil droplets of the oil-in-water emulsified product constituting the composition has an average particle size of 150 nm or less, thickening with hydrophobically modified ethoxylated urethane achieves a synergistic thickening effect, providing a jelly having a jiggling touch. This jelly causes no reduction in the viscosity even at 50° C. (Examples 1 to 4).

For Comparative Example 15 in which emulsified oil droplets have a particle size of more than 150 nm, thickening and creaming by the laminated structure of the gel composed of an amphiphile-surfactant-water system have been observed, but a thickening effect due to the synergistic effect provided in the present invention and a jiggling unique texture are not achieved.

TABLE 4

|  | Example 5 | Example 6 | Example 7 | Example 2 | Example 8 | Example 9 | Example 10 |
|---|---|---|---|---|---|---|---|
| 1) Ion exchanged water | 19.2 | 19.2 | 19.2 | 19.2 | 19.2 | 19.2 | 19.2 |
| 2) Sodium stearoyl glutamate | 0.1 | 0.2 | 0.4 | 0.6 | 0.8 | 1 | 1.2 |
| 3) Dipropylene glycol | 0.5 | 1 | 2 | 3 | 4 | 5 | 6 |
| 4) Glycerin | 0.2 | 0.4 | 0.8 | 1.2 | 1.6 | 2 | 2.4 |
| 5) Behenyl alcohol | 0.167 | 0.33 | 0.67 | 1 | 1.33 | 1.67 | 2 |
| 6) Stearyl alcohol | 0.167 | 0.33 | 0.67 | 1 | 1.33 | 1.67 | 2 |
| 7) Hydrogenated polydecene | 0.67 | 1.33 | 2.67 | 4 | 5.33 | 6.67 | 8 |
| 8) Hydrophobically modified ethoxylated urethane | 1 | 1 | 1 | 1 | 1 | 1 | 1 |
| 9) Ion exchanged water | Quantum sufficit | Quantum sufficit | Quantum sufficit | Quantum sufficit | Quantum sufficit | Quantum sufficit | Quantum sufficit |
| 10) Dipropylene glycol | 6.5 | 6 | 5 | 4 | 3 | 2 | 1 |
| 11) Glycerin | 2.8 | 2.6 | 2.2 | 1.8 | 1.4 | 1 | 0.6 |
| 12) Ion exchanged water | Balance | Balance | Balance | Balance | Balance | Balance | Balance |
| Total | 100 | 100 | 100 | 100 | 100 | 100 | 100 |
| Appearance | Translucent | Translucent | Translucent | Translucent | Translucent | Slightly whitely turbid | Slightly whitely turbid |
| Jiggly feeling | B | A | A | A | A | A | A |
| Emulsified particle size/nm | 63.2 | 63.2 | 63.2 | 63.2 | 63.2 | 63.2 | 63.2 |
| Viscosity cp 1 s$^{-1}$/Pa · s | 8.21 | 12.8 | 30.9 | 43.2 | 54.9 | 51.8 | 56.0 |
| Viscosity cp 10 s$^{-1}$/Pa · s | 1.17 | 1.27 | 3.48 | 6.01 | 7.43 | 8.89 | 9.47 |
| Thickening properties at 50° C. | C | B | A | A | A | A | A |

Production Method:

In the same manner as in Example 1, a mixture prepared by dissolving 5) to 7) under heating at 80° C. was mixed under stirring into a product prepared by dissolving 1) to 4) under heating at 75° C., and the resulting mixture was high-pressure emulsified under a pressure of about 100 MPa. Thereafter, the high-pressure emulsified product was diluted with a constant amount of a mixture of 10) to 12) and then thickened with a hydrophobically modified ethoxylated urethane aqueous solution.

As shown in Table 4, in the range of the amount of the oil component blended in Examples 5 to 10 (0.67 to 8% by mass), it was possible to achieve a jiggling texture and viscosity stability at high-temperatures. That is, even Example 5 will not particularly cause a practical problem. In order to further suppress reduction in the viscosity at high temperatures, for example, it is only required that the amount of the oil component blended be 1% by mass or more.

TABLE 5

|  | Example 11 | Example 12 | Example 2 | Example 13 | Example 14 | Example 15 |
|---|---|---|---|---|---|---|
| 1) Ion exchanged water | 19.2 | 19.2 | 19.2 | 19.2 | 19.2 | 192 |
| 2) Sodium stearoyl glutamate | 0.6 | 0.6 | 0.6 | 0.6 | 0.6 | 0.6 |
| 3) Dipropylene glycol | 3 | 3 | 3 | 3 | 3 | 3 |
| 4) Glycerin | 1.2 | 1.2 | 1.2 | 1.2 | 1.2 | 1.2 |
| 5) Behenyl alcohol | 1 | 1 | 1 | 1 | 1 | 1 |
| 6) Stearyl alcohol | 1 | 1 | 1 | 1 | 1 | 1 |
| 7) Hydrogenated polydecene | 4 | 4 | 4 | 4 | 4 | 4 |
| 8) Hydrophobically modified ethoxylated urethane | 0.6 | 0.8 | 1 | 1.3 | 1.5 | 2.0 |
| 9) Ion exchanged water | Quantum sufficit | Quantum sufficit | Quantum sufficit | Quantum sufficit | Quantum sufficit | Quantum sufficit |
| 10) Dipropylene glycol | 4 | 4 | 4 | 4 | 4 | 4 |
| 11) Glycerin | 1.8 | 1.8 | 1.8 | 1.8 | 1.8 | 1.8 |
| 12) Ion exchanged water | Balance | Balance | Balance | Balance | Balance | Balance |
| Total | 100 | 100 | 100 | 100 | 100 | 100 |
| Appearance | Translucent | Translucent | Translucent | Translucent | Slightly whitely turbid | Slightly whitely turbid |
| Jiggly feeling | B | A | A | A | A | A |
| Emulsified particle size/nm | 63.2 | 63.2 | 63.2 | 63.2 | 63.2 | 63.2 |
| Viscosity cp 1 $s^{-1}$/Pa · s | 7.04 | 32.1 | 43.2 | 35.5 | 46.6 | 77.7 |
| Viscosity cp 10 $s^{-1}$/Pa · s | 0.73 | 3.83 | 6.01 | 10.0 | 10.8 | 16.4 |
| Thickening properties at 50° C. | B | A | A | A | A | A |

Production Method:

In the same manner as in Example 1, a mixture prepared by dissolving 5) to 7) under heating at 80° C. was mixed under stirring into a product prepared by dissolving 1) to 4) under heating at 75° C., and the resulting mixture was high-pressure emulsified under a pressure of about 100 MPa. Thereafter, the high-pressure emulsified product was diluted with a constant amount of a mixture of 10) to 12) and then thickened with a hydrophobically modified ethoxylated urethane aqueous solution.

As shown in Table 5, in the range of the amount of the hydrophobically modified ethoxylated urethane blended in Examples 11 to 15 (0.6 to 2.0% by mass), it was possible to achieve a jiggling texture and viscosity stability at high-temperatures.

TABLE 6

|  | Example 16 | Example 17 | Example 18 | Example 19 | Example 20 | Example 21 | Example 22 |
|---|---|---|---|---|---|---|---|
| 1) Ion exchanged water | 22.8 | 22.8 | 22.8 | 19.2 | 19.2 | 19.2 | 19.2 |

TABLE 6-continued

| | Example 16 | Example 17 | Example 18 | Example 19 | Example 20 | Example 21 | Example 22 |
|---|---|---|---|---|---|---|---|
| 2) Alkyl trimethyl ammonium chloride | — | — | — | 0.4 | 0.4 | 0.56 | 0.56 |
| 3) Dipropylene glycol | 1 | 1 | 1 | — | — | — | — |
| 4) Glycerin | 2.13 | 2.13 | 2.13 | — | — | — | — |
| 5) Alkylcarboxy-modified trisiloxane | 1 | 1 | 1 | — | — | — | — |
| 6) Polyoxyethylene glyceryl monostearate | 2.13 | 2.13 | 2.13 | — | — | — | — |
| 7) Triethanolamine | 0.44 | 0.44 | 0.44 | — | — | — | — |
| 8) Behenyl alcohol | 1.5 | 1.5 | 1.5 | 1 | 1 | 1 | 1 |
| 9) Stearyl alcohol | — | — | — | 1 | 1 | 1 | 1 |
| 10) Hydrogenated polydecene | 3 | 3 | 3 | 2 | 2 | 4 | 4 |
| 11) Dimethyl polysiloxane | 3 | 3 | 3 | 2 | 2 | — | — |
| 12) Hydrophobically modified ethoxylated urethane | 0.4 | 0.7 | 1 | 1 | 1.5 | 1 | 1.5 |
| 13) Ion exchanged water | Quantum sufficit | Quantum sufficit | Quantum sufficit | Quantum sufficit | Quantum sufficit | Quantum sufficit | Quantum sufficit |
| 14) Dipropylene glycol | — | — | — | 4 | 4 | 4 | 4 |
| 15) Ion exchanged water | Balance | Balance | Balance | Balance | Balance | Balance | Balance |
| Total | 100 | 100 | 100 | 100 | 100 | 100 | 100 |
| Appearance | Translucent | Slightly whitely turbid | Slightly whitely turbid | Translucent | Translucent | Translucent | Translucent |
| Jiggly feeling | B | A | A | A | A | A | A |
| Emulsified particle size/nm | 70 | 72 | 72 | 88.1 | 88.1 | 76.4 | 76.4 |
| Viscosity cp 1 s$^{-1}$/Pa · s | 40.5 | 41.3 | 55.3 | 34.0 | 41.2 | 39.1 | 34.3 |
| Viscosity cp 10 s$^{-1}$/Pa · s | 4.28 | 8.26 | 12.2 | 3.06 | 9.93 | 9.2 | 12.7 |
| Thickening properties at 50° C. | B | A | A | A | A | A | A |

Production Method:

A mixture prepared by dissolving the corresponding ingredients from 5) to 11) under heating at 80° C. was mixed under stirring into a product prepared by dissolving the corresponding ingredients from 1) to 4) under heating at 75° C., and the resulting mixture was high-pressure emulsified under a pressure of about 100 MPa (the high-pressure emulsifying apparatus was as described above). Subsequently, the high-pressure emulsified product was diluted with a constant amount of a mixture of 14) and 15) and then thickened with a hydrophobically modified ethoxylated urethane aqueous solution.

The results shown in Table 6 indicate that the jiggling touch and the viscosity stability at high temperatures intended by the present invention are achieved even if the type of the surfactant and the oil component used in the oil-in-water emulsified product constituting the composition of the present invention is changed.

FIG. 1 is a graph formed by plotting the storage modulus (G') and loss modulus (G") values at a frequency of 1 Hz and under a 1% strain when the temperature was changed against temperatures.

In Comparative Example 8, it is construed that, around 40° C., the magnitudes of G' and G" are inverted and the gel transfers into a sol. Also in Comparative Example 15, the transition point from the gel to a sol is observed between 50° C. and 60° C. In contrast to these, in Example 1 according to the present invention, G' is larger than G" even at 60° C., and a fact has been supported that the gel state is maintained even at high temperatures.

Formulation examples of the cosmetics containing the elastic jelly-like composition of the present invention as their base will be now described, but the present invention is not limited to these examples. Incidentally, the cosmetics described in the following formulation examples had a jiggling texture and viscosity stability at high temperatures based on the thickening jelly-like composition of the present invention.

(Example 23) Essence

Formulation

| | |
|---|---|
| 1) Purified water | quantum sufficit |
| 2) Sodium stearoyl glutamate | 0.6 |
| 3) Dipropylene glycol | 4.7 |
| 4) Glycerin | 8 |
| 5) Behenyl alcohol | 0.7 |
| 6) Stearyl alcohol | 0.6 |
| 7) Cetostearyl alcohol | 0.6 |
| 8) Hydrogenated polydecene | 4 |
| 9) Pentaerythritol tetra 2-ethylhexanoate | 2 |
| 10) Phytosteryl macadamiate | 0.2 |
| 11) Petrolatum | 0.5 |
| 12) Dimethyl polysiloxane | 1 |
| 13) Fragrance | quantum sufficit |
| 14) (PEG-240/decyltetradeceth-20/HDI) copolymer | 1 |
| 15) Purified water | balance |

<Preparation Method>

A mixture prepared by dissolving 5) to 13) under heating at 80° C. was mixed under stirring into a product prepared by dissolving 1) to 4) under heating at 75° C., and the resulting mixture was high-pressure emulsified under a pressure of about 100 MPa. Thereafter the high-pressure emulsified product was thickened with a hydrophobically modified ethoxylated urethane aqueous solution.

(Example 24) Jelly Cream

Formulation

| | |
|---|---|
| 1) Purified water | quantum sufficit |
| 2) Dipropylene glycol | 6 |
| 3) Alkylcarboxy-modified trisiloxane | 1 |
| 4) Polyoxyethylene glyceryl monostearate | 2.1 |
| 5) Triethanolamine | 0.4 |
| 6) Behenyl alcohol | 1.5 |
| 7) Dimethyl polysiloxane | 0.6 |
| 8) Hydrogenated polydecene | 3 |
| 9) Fragrance | quantum sufficit |
| 10) (PEG-240/decyltetradeceth-20/HDI) copolymer | 1 |
| 11) Purified water | balance |

<Preparation Method>

A mixture prepared by dissolving 3) to 9) under heating at 80° C. was mixed under stirring into a product prepared by heating 1) and 2) at 75° C., and the resulting mixture was high-pressure emulsified under a pressure of about 100 MPa. Thereafter the high-pressure emulsified product was thickened with a hydrophobically modified ethoxylated urethane aqueous solution.

(Example 25) Massage Jelly

Formulation

| | |
|---|---|
| 1) Purified water | quantum sufficit |
| 2) Sodium stearoyl glutamate | 0.6 |
| 3) Dipropylene glycol | 4.7 |
| 4) Glycerin | 8 |
| 5) Polyethylene glycol 400 | 0.2 |
| 6) Citric acid | 0.01 |
| 7) Sodium citrate | 0.04 |
| 8) Behenyl alcohol | 0.7 |
| 9) Stearyl alcohol | 0.6 |
| 10) Cetostearyl alcohol | 0.6 |
| 11) Hydrogenated polydecene | 4 |
| 12) Meadowfoam oil | 2 |
| 13) Octyl methoxycinnamate | 3 |
| 14) Petrolatum | 0.5 |
| 15) Dimethyl polysiloxane | 1 |
| 16) Fragrance | 0.05 |
| 17) (PEG-240/decyltetradeceth-20/HDI) copolymer | 1 |
| 18) Purified water | balance |

<Preparation Method>

A mixture prepared by dissolving 8) to 16) under heating at 80° C. was mixed under stirring into a product prepared by dissolving 1) to 7) under heating at 75° C., and the resulting mixture was high-pressure emulsified under a pressure of about 100 MPa. Thereafter the high-pressure emulsified product was thickened with a hydrophobically modified ethoxylated urethane aqueous solution.

(Example 26) Hair Cream

Formulation

| | |
|---|---|
| 1) Purified water | quantum sufficit |
| 2) Alkyl trimethyl ammonium chloride | 0.6 |
| 3) Dipropylene glycol | 3 |
| 4) Glycerin | 1.2 |
| 5) Behenyl alcohol | 1 |
| 6) Stearyl alcohol | 0.5 |
| 7) Cetostearyl alcohol | 0.5 |
| 8) Hydrogenated polydecene | 3 |
| 9) Dimethyl polysiloxane | 3 |
| 10) Petrolatum | 1 |
| 11) Fragrance | quantum sufficit |
| 12) (PEG-240/decyltetradeceth-20/HDI) copolymer | 1 |
| 13) Cationized cellulose | 0.5 |
| 14) Purified water | balance |

<Preparation Method>

A mixture prepared by dissolving 5) to 11) under heating at 80° C. was mixed under stirring into a product prepared by dissolving 1) to 4) under heating at 75° C., and the resulting mixture was high-pressure emulsified under a pressure of about 100 MPa. Thereafter, the high-pressure emulsified product was thickened with a constant amount of the hydrophobically modified ethoxylated urethane, and a cationized cellulose aqueous solution was added thereto.

(Example 27) Hair Jelly

Formulation

| | |
|---|---|
| 1) Purified water | quantum sufficit |
| 2) Alkyl trimethyl ammonium chloride | 0.6 |
| 3) Dipropylene glycol | 3 |
| 4) 1,3-Buthylene glycol | 2 |
| 5) Glycerin | 1.2 |
| 6) Ethanol | 5 |
| 7) Stearyl alcohol | 0.5 |
| 8) Behenyl alcohol | 0.5 |
| 9) Hydrogenated polydecene | 3 |
| 10) Dimethyl polysiloxane | 3 |
| 11) Fragrance | quantum sufficit |
| 12) (PEG-240/decyltetradeceth-20/HDI) copolymer | 1 |
| 13) Purified water | balance |

<Preparation Method>

A mixture prepared by dissolving 7) to 11) under heating at 80° C. was mixed under stirring into a product prepared by dissolving 1) to 6) under heating at 75° C., and the resulting mixture was high-pressure emulsified under a pressure of about 100 MPa. Thereafter the high-pressure emulsified product was thickened with a hydrophobically modified ethoxylated urethane aqueous solution.

(Example 28) Mascara

Formulation

| | |
|---|---|
| 1) Purified water | quantum sufficit |
| 2) Sodium stearoyl glutamate | 2.6 |
| 3) Behenyl alcohol | 4.3 |
| 4) Stearyl alcohol | 4.3 |
| 5) Light isoparaffin | 6 |
| 6) Dimethyl polysiloxane | 1 |
| 7) Decamethylcyclopentasiloxane | 5 |
| 8) Trimethylsiloxysilicate | 5 |
| 9) Purified water | balance |
| 10) (PEG-240/decyltetradeceth-20/HDI) copolymer | 1 |
| 11) Methyl polysiloxane emulsion | quantum sufficit |
| 12) Isopropanol | 3 |
| 13) 1,3-Buthylene glycol | 6 |
| 14) Sodium hydrogen carbonate | 0.01 |
| 15) DL-α-Tocopherol acetate | 0.1 |
| 16) Sodium acetylated hyaluronate | 0.1 |
| 17) para-Hydroxybenzoate | quantum sufficit |
| 18) Phenoxyethanol | 0.3 |
| 19) Black iron oxide | 8 |
| 20) Polyvinyl alcohol | 4 |
| 21) Alkyl acrylate copolymer emulsion | 12 |
| 22) Polyvinyl acetate emulsion | 12 |
| 23) Nylon fiber (1 to 2 mm) | 6 |
| 24) Anhydrous silicate | 0.5 |
| 25) Titanium oxide | 1 |
| 26) Fragrance | quantum sufficit |

<Preparation Method>

A mixture prepared by mixing 3) to 8) under stirring at 80° C. was mixed under stirring into a product prepared by dissolving 1) and 2) under heating at 75° C., and the resulting mixture was high-pressure emulsified under a pressure of about 100 MPa. The high-pressure emulsified product was diluted with a constant amount of a mixture of 9) and 10) and then 11) to 26) were mixed thereto.

For high-pressure emulsification, a Nanomizer mark II (manufactured by YOSHIDA KIKAI CO., LTD.) was used, and for stirring mixing, an H-20 type Homogenizer (manufactured by SANWA ENGINEERING CO., LTD.) was used.

(Example 29) Mascara

Formulation

| | |
|---|---|
| 1) Purified water | quantum sufficit |
| 2) Sodium stearoyl glutamate | 2.3 |
| 3) Behenyl alcohol | 3.8 |
| 4) Stearyl alcohol | 3.8 |
| 5) Microcrystalline wax | 6 |
| 6) Sucrose fatty acid ester | 9 |
| 7) Purified water | balance |
| 8) (PEG-240/decyltetradeceth-20/HDI) copolymer | 1 |
| 9) Methyl polysiloxane emulsion | quantum sufficit |
| 10) Isopropanol | 3 |
| 11) Batyl alcohol | 1 |
| 12) Dipropylene glycol | 5 |
| 13) N-lauroyl-L-glutamate di(phytosteryl 2-octyldodecyl) | 0.1 |
| 14) Isobutylene-sodium maleate copolymer solution | 0.1 |
| 15) Mica titanium | 1 |
| 16) Sodium hydrogen carbonate | 0.1 |
| 17) DL-α-Tocopherol acetate | 0.1 |
| 18) para-Hydroxybenzoate | quantum sufficit |
| 19) Sodium dehydroacetate | quantum sufficit |
| 20) Phenoxyethanol | quantum sufficit |
| 21) Black iron oxide | 10 |
| 22) Sea weed extract | 0.1 |
| 23) Aluminum magnesium silicate | 0.1 |
| 24) Polyalkyl acrylate emulsion | 5 |
| 25) Polyvinyl alcohol | 0.5 |
| 26) Polyvinyl acetate emulsion | 7 |
| 27) Anhydrous silicate | 0.5 |
| 28) Titanium oxide | 0.1 |

<Preparation Method>

A mixture prepared by mixing 3) to 6) under stirring at 90° C. was mixed under stirring into a product prepared by dissolving 1) and 2) under heating at 75° C., and the resulting mixture was high-pressure emulsified under a pressure of about 100 MPa. The high-pressure emulsified product was diluted with a constant amount of a mixture of 7) and 8) and then 9) to 28) were mixed thereto.

For high-pressure emulsification, a Nanomizer mark II (manufactured by YOSHIDA KIKAI CO., LTD.) was used, and for stirring mixing, an H-20 type Homogenizer (manufactured by SANWA ENGINEERING CO., LTD.) was used.

(Example 30) Mascara Base

Formulation

| | |
|---|---|
| 1) Purified water | quantum sufficit |
| 2) Sodium stearoyl glutamate | 3.3 |
| 3) Behenyl alcohol | 5.5 |
| 4) Stearyl alcohol | 5.5 |
| 5) Microcrystalline wax | 10 |
| 6) White beeswax | 10 |
| 7) Heavy liquid paraffin | 2 |
| 8) Purified water | balance |
| 9) (PEG-240/decyltetradeceth-20/HDI) copolymer | 1 |
| 10) Methyl polysiloxane emulsion | quantum sufficit |
| 11) Isopropanol | 3 |
| 12) 1,3-Buthylene glycol | 7 |
| 13) Isobutylene-sodium maleate copolymer solution | 0.1 |
| 14) Talc | 1 |
| 15) para-Hydroxybenzoate | quantum sufficit |
| 16) Sea weed extract | 0.1 |
| 17) Alkyl acrylate copolymer emulsion | 22 |
| 18) Polyvinyl alcohol | 2 |
| 19) Nylon fiber (1 to 2 mm) | 5 |

<Preparation Method>

A mixture prepared by mixing 3) to 7) under stirring at 90° C. was mixed under stirring into a product prepared by dissolving 1) and 2) under heating at 75° C., and the resulting mixture was high-pressure emulsified under a pressure of about 100 MPa. The high-pressure emulsified product was diluted with a constant amount of a mixture of 8) and 9) and then 10) to 19) were mixed thereto.

For high-pressure emulsification, a Nanomizer mark II (manufactured by YOSHIDA KIKAI CO., LTD.) was used, and for stirring mixing, an H-20 type Homogenizer (manufactured by SANWA ENGINEERING CO., LTD.) was used.

(Example 31) Eyeliner

Formulation

| | |
|---|---|
| 1) Purified water | quantum sufficit |
| 2) Sodium stearoyl glutamate | 0.8 |

-continued

| | | |
|---|---|---|
| 3) Behenyl alcohol | 1.3 | |
| 4) Stearyl alcohol | 1.3 | |
| 5) Liquid paraffin | 5 | |
| 6) Purified water | balance | |
| 7) (PEG-240/decyltetradeceth-20/HDI) copolymer | 1 | |
| 8) Methyl polysiloxane emulsion | quantum sufficit | |
| 9) Glycerin | 3 | |
| 10) 1,3-Butylene glycol | 5 | |
| 11) Isobutylene-sodium maleate copolymer solution | 1 | |
| 12) Titanium oxide | quantum sufficit | |
| 13) Platy barium sulfate | quantum sufficit | |
| 14) Kaolin | 8 | |
| 15) Black iron oxide-coated mica titanium (pearlizing agent) | 3 | |
| 16) Black iron oxide | 9 | |
| 17) DL-α-Tocopherol acetate | 0.1 | |
| 18) para-Hydroxybenzoate | quantum sufficit | |
| 19) Alkyl acrylate copolymer emulsion | 7 | |

<Preparation Method>

A mixture prepared by mixing 3) to 5) under stirring at 80° C. was mixed under stirring into a product prepared by dissolving 1) and 2) under heating at 75° C., and the resulting mixture was high-pressure emulsified under a pressure of about 100 MPa. The high-pressure emulsified product was diluted with a constant amount of a mixture of 6) and 7) and then 8) to 19) were mixed thereto.

For high-pressure emulsification, a Nanomizer mark II (manufactured by YOSHIDA KIKAI CO., LTD.) was used, and for stirring mixing, an H-20 type Homogenizer (manufactured by SANWA ENGINEERING CO., LTD.) was used.

(Example 32) Makeup Remover

Formulation

| | |
|---|---|
| 1) Purified water | quantum sufficit |
| 2) Sodium stearoyl glutamate | 3.9 |
| 3) Behenyl alcohol | 6.5 |
| 4) Stearyl alcohol | 6.5 |
| 5) Decamethylcyclopentasiloxane | 25 |
| 6) Jojoba oil | 0.1 |
| 7) Rice germ oil | 0.1 |
| 8) Neopentyl glycol dicaprate | 10 |
| 9) Cetyl 2-ethylhexanoate | 3 |
| 10) Purified water | balance |
| 11) (PEG-240/decyltetradeceth-20/HDI) copolymer | 1 |
| 12) 1,3-Buthylene glycol | 10 |
| 13) Potassium hydroxide | 0.1 |
| 14) Royal jelly extract | 0.1 |
| 15) para-Hydroxybenzoate | quantum sufficit |
| 16) Edetate trisodium | 0.1 |

<Preparation Method>

A mixture prepared by mixing 3) to 9) under stirring at 80° C. was mixed under stirring into a product prepared by dissolving 1) and 2) under heating at 75° C., and the resulting mixture was high-pressure emulsified under a pressure of about 100 MPa. The high-pressure emulsified product was diluted with a constant amount of a mixture of 10) and 11) and then 12) to 16) were mixed into the diluted emulsified product.

For high-pressure emulsification, a Nanomizer mark II (manufactured by YOSHIDA KIKAI CO., LTD.) was used, and for stirring mixing, an H-20 type Homogenizer (manufactured by SANWA ENGINEERING CO., LTD.) was used.

(Example 33) Eyeshadow

Formulation

| | |
|---|---|
| 1) Purified water | quantum sufficit |
| 2) Sodium stearoyl glutamate | 3.2 |
| 3) Behenyl alcohol | 5.3 |
| 4) Stearyl alcohol | 5.3 |
| 5) Decamethylcyclopentasiloxane | 16 |
| 6) Methyl phenyl polysiloxane | 0.5 |
| 7) Trimethylsiloxysilicate | 4.5 |
| 8) Purified water | balance |
| 9) (PEG-240/decyltetradeceth-20/HDI) copolymer | 1 |
| 10) Methyl polysiloxane emulsion | 4.5 |
| 11) 1,3-Buthylene glycol | 5 |
| 12) DL-α-Tocopherol acetate | 0.1 |
| 13) para-Hydroxybenzoate | quantum sufficit |
| 14) Phenoxyethanol | 0.2 |
| 15) Anhydrous silicate | 1.5 |
| 16) Titanium oxide | 1.7 |
| 17) Colcothar | 1 |
| 18) Mica | 9 |
| 19) Fragrance | quantum sufficit |

<Preparation Method>

A mixture prepared by mixing 3) to 7) under stirring at 80° C. was mixed under stirring into a product prepared by dissolving 1) and 2) under heating at 75° C., and the resulting mixture was high-pressure emulsified under a pressure of about 100 MPa. The high-pressure emulsified product was diluted with a constant amount of a mixture of 8) and 9) and then 10) to 19) were mixed thereto.

For high-pressure emulsification, a Nanomizer mark H (manufactured by YOSHIDA KIKAI CO., LTD.) was used, and for stirring mixing, an H-20 type Homogenizer (manufactured by SANWA ENGINEERING CO., LTD.) was used.

(Example 34) Liquid Rouge

Formulation

| | |
|---|---|
| 1) Purified water | quantum sufficit |
| 2) Sodium stearoyl glutamate | 3.2 |
| 3) Behenyl alcohol | 5.3 |
| 4) Stearyl alcohol | 5.3 |
| 5) Hydrogenated polydecene | 21 |
| 6) Purified water | balance |
| 7) (PEG-240/decyltetradeceth-20/HDI) copolymer | 1 |
| 8) Alkyl acrylate copolymer emulsion | 12 |
| 9) 1,3-Buthylene glycol | 5 |
| 10) DL-α-Tocopherol acetate | 0.1 |
| 11) para-Hydroxybenzoate | quantum sufficit |
| 12) Phenoxyethanol | 0.2 |
| 13) Acid fuchsin | 0.1 |
| 14) Fragrance | quantum sufficit |

<Preparation Method>

A mixture prepared by mixing 3) to 5) under stirring at 80° C. was mixed under stirring into a product prepared by dissolving 1) and 2) under heating at 75° C., and the resulting mixture was high-pressure emulsified under a pressure of about 100 MPa. The high-pressure emulsified product was diluted with a constant amount of a mixture of 6) and 7) and then 8) to 14) were mixed thereto.

For high-pressure emulsification, a Nanomizer mark II (manufactured by YOSHIDA KIKAI CO., LTD.) was used, and for stirring mixing, an H-20 type Homogenizer (manufactured by SANWA ENGINEERING CO., LTD.) was used.

The invention claimed is:

1. An oil-in-water emulsified elastic composition having a jiggling texture, the composition comprising:
    an oil phase in the form of droplets having an average particle size of 150 nm or less; and
    a water phase comprising 0.4 to 10% by mass, relative to the total amount of the composition, of a hydrophobically modified ethoxylated urethane;
    wherein the oil droplets comprise an α-gel consisting of a higher alcohol having a carbon chain length of 16 or more, an oil component, and a surfactant selected from cationic and anionic surfactants.

2. The composition according to claim 1, wherein: the hydrophobically modified ethoxylated urethane is represented by the following formula (I):

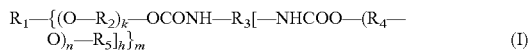  (I)

wherein $R_1$, $R_2$, and $R_4$ each independently represent a hydrocarbon group having 2 to 4 carbon atoms; $R_3$ represents a hydrocarbon group having 1 to 10 carbon atoms; $R_5$ represents a hydrocarbon group having 8 to 36 carbon atoms; m is a number of 2 or more; h is a number of 1 or more; k is a number of 1 to 500; and n is a number of 1 to 200.

3. The composition according to claim 2, wherein: the hydrophobically modified ethoxylated urethane is the urethane having INCI name PEG-240/HDI copolymer bis-decyltetradeceth-20 ether.

4. A cosmetic base comprising: the composition according to claim 1.

* * * * *